US012578916B2

(12) United States Patent
Gibby et al.

(10) Patent No.: US 12,578,916 B2
(45) Date of Patent: Mar. 17, 2026

(54) COLLABORATION USING AR HEADSETS

(71) Applicant: Novarad Corporation, Provo, UT (US)

(72) Inventors: Wendell Arlen Gibby, Mapleton, UT (US); Steven Todd Cvetko, Draper, UT (US); Joel Steven Lyons, Springville, UT (US); Garrett David Roberts, American Fork, UT (US)

(73) Assignee: Novarad Corporation, Provo, UT (US)

( * ) Notice: Subject to any disclaimer, the term of this patent is extended or adjusted under 35 U.S.C. 154(b) by 0 days.

(21) Appl. No.: 18/820,167

(22) Filed: Aug. 29, 2024

(65) Prior Publication Data

US 2026/0064349 A1 Mar. 5, 2026

(51) Int. Cl.
| | |
|---|---|
| *G06F 3/14* | (2006.01) |
| *G06F 3/01* | (2006.01) |
| *G06F 3/04815* | (2022.01) |
| *G06F 3/04842* | (2022.01) |
| *G06F 3/04845* | (2022.01) |
| *G06F 3/16* | (2006.01) |
| *G16H 40/67* | (2018.01) |
| *G16H 80/00* | (2018.01) |
| *H04L 65/1093* | (2022.01) |
| *H04L 65/403* | (2022.01) |

(52) U.S. Cl.
CPC ............ *G06F 3/1454* (2013.01); *G06F 3/012* (2013.01); *G06F 3/04815* (2013.01); *G06F 3/04842* (2013.01); *G06F 3/04845* (2013.01); *G06F 3/167* (2013.01); *G16H 40/67*

(2018.01); *G16H 80/00* (2018.01); *H04L 65/1093* (2013.01); *H04L 65/403* (2013.01)

(58) Field of Classification Search
CPC .... G06F 3/1454; G06F 3/012; G06F 3/04815; G06F 3/04842; G06F 3/04845; G06F 3/167; G16H 40/67; G16H 80/00; H04L 65/1093; H04L 65/403
See application file for complete search history.

(56) References Cited

U.S. PATENT DOCUMENTS

2019/0365498 A1* 12/2019 Gibby ..................... A61B 90/90
2022/0255995 A1* 8/2022 Berliner .................. H04W 4/80

* cited by examiner

*Primary Examiner* — Andrey Belousov
(74) *Attorney, Agent, or Firm* — Thorpe North & Western, LLP.; Steve M. Perry

(57) ABSTRACT

Technology is described for a method of enabling a joining user to share a collaboration group, which includes at least one collaboration user. The collaboration group may jointly view an image data set aligned with a body of a person using AR headsets. The method may include detecting a topology of an operating room using a sensor of the joining user's AR headset. The topology of the operating room recorded by the joining user's AR headset may be compared to an operating room topology previously recorded for the collaboration group to determine whether the joining user and the collaboration group are occupying the same operating room. The joining user may be allowed to join the collaboration group, based in part on the same operating room being detected.

45 Claims, 10 Drawing Sheets

100

106

108 —— 110

122

102

Collaboration
User

104

120

Collaboration
User

136

Patient

132

130

Wireless
Access Point

Joining User

134

Server
140

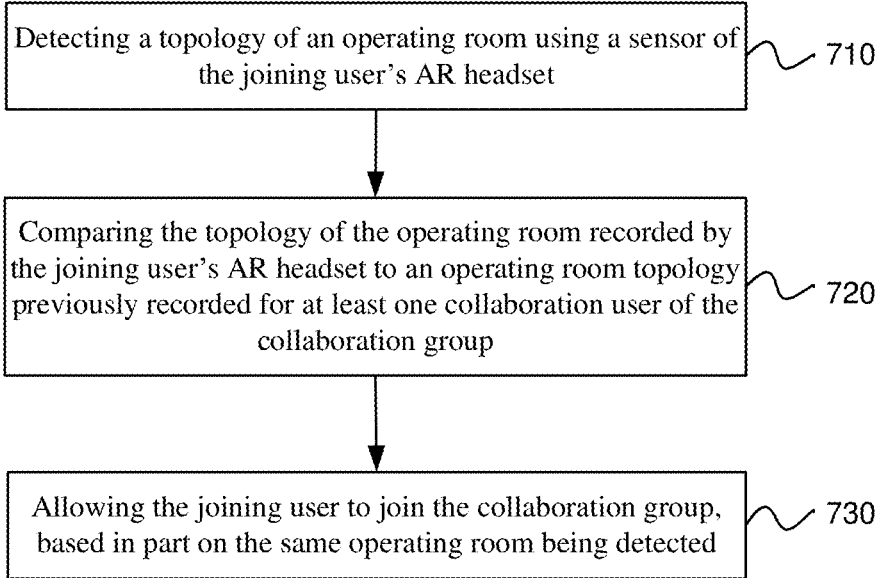

Detecting a topology of an operating room using a sensor of the joining user's AR headset ⌇ 710

Comparing the topology of the operating room recorded by the joining user's AR headset to an operating room topology previously recorded for at least one collaboration user of the collaboration group ⌇ 720

Allowing the joining user to join the collaboration group, based in part on the same operating room being detected ⌇ 730

FIG. 7

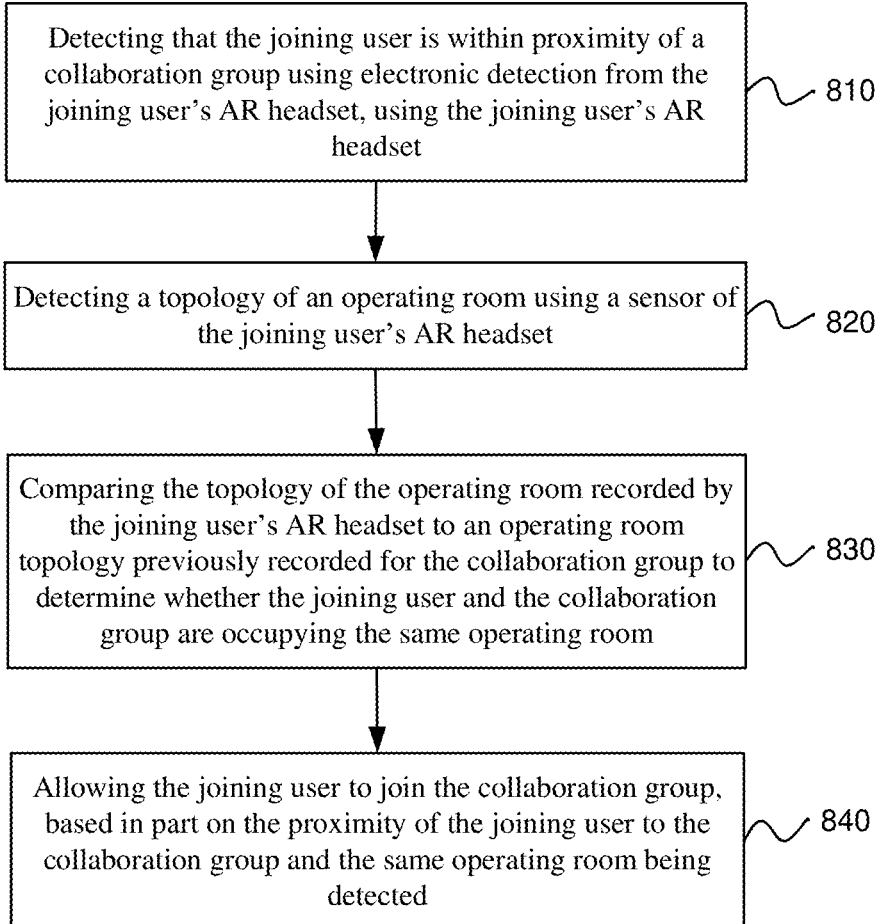

Detecting that the joining user is within proximity of a collaboration group using electronic detection from the joining user's AR headset, using the joining user's AR headset      810

Detecting a topology of an operating room using a sensor of the joining user's AR headset      820

Comparing the topology of the operating room recorded by the joining user's AR headset to an operating room topology previously recorded for the collaboration group to determine whether the joining user and the collaboration group are occupying the same operating room      830

Allowing the joining user to join the collaboration group, based in part on the proximity of the joining user to the collaboration group and the same operating room being detected      840

FIG. 8

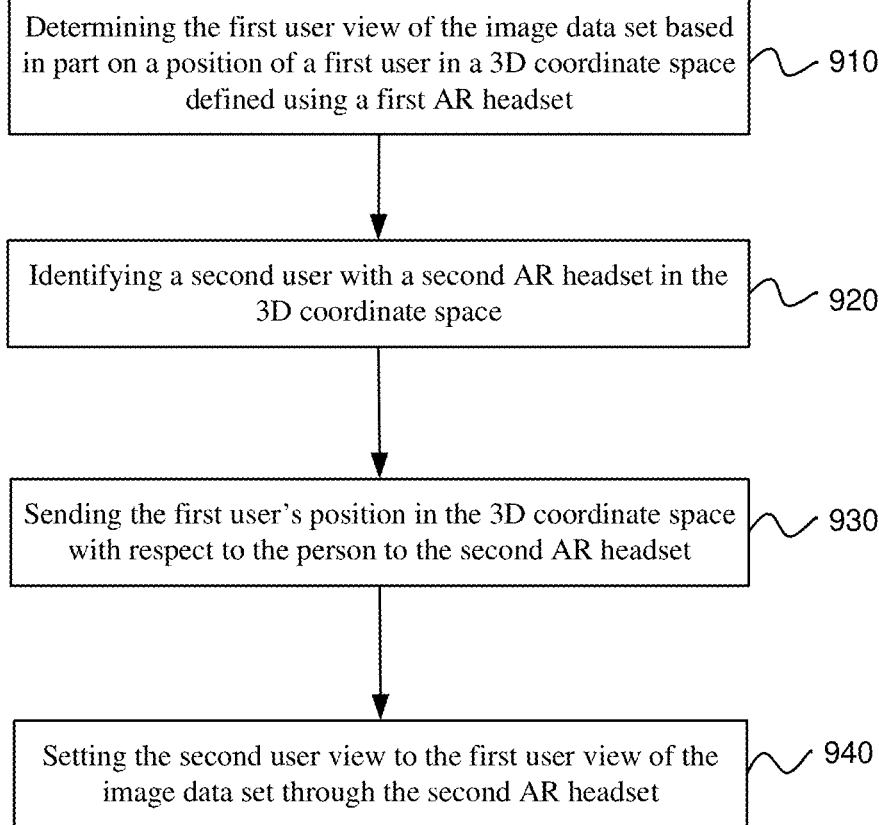

Determining the first user view of the image data set based in part on a position of a first user in a 3D coordinate space defined using a first AR headset ⟋ 910

Identifying a second user with a second AR headset in the 3D coordinate space ⟋ 920

Sending the first user's position in the 3D coordinate space with respect to the person to the second AR headset ⟋ 930

Setting the second user view to the first user view of the image data set through the second AR headset ⟋ 940

FIG. 9

COLLABORATION USING AR HEADSETS

BACKGROUND

Mixed or augmented reality is an area of computing technology where views from the physical world and images from virtual computing worlds may be combined into a mixed reality view for a user. In mixed reality, people, places, and objects from the physical world and virtual worlds become a blended visual and audio environment. A mixed reality experience may be provided through existing commercial or custom software along with the use of VR (virtual reality) or AR (augmented reality) headsets.

Augmented reality (AR) is an example of mixed reality where a live direct view (or an indirect view) of a physical, real-world environment is augmented or supplemented by computer-generated sensory input such as sound, video, graphics or other data. Augmentation is performed as a real-world location is viewed and in context with environmental elements. With the help of AR technology (e.g. adding computer vision and object recognition) the information about the surrounding real world of the user may become interactive and may be digitally modified.

BRIEF DESCRIPTION OF THE DRAWINGS

FIG. 7 is a flowchart illustrating an example method for enabling a joining user to share a collaboration group with at least one collaboration user, and for viewing an image data set aligned with a body of a person.

FIG. 8 is a flowchart illustrating an example method for enabling a joining user to share a collaboration group with at least one collaboration user, and for viewing an image data set aligned with a body of a person.

FIG. 9 is a flowchart illustrating an example method for managing a first user view and a second user view of an image data set.

DETAILED DESCRIPTION

Figure 1:
FIG. 1 is a diagram illustrating a system and method for enabling a joining user to share a collaboration group.

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated, which would occur to one skilled in the relevant art and having possession of this disclosure, are to be considered within the scope of the description.

A technology is described that may provide the ability for a user or a joining user with an AR headset to securely join a collaboration group that has one or more collaboration users. The collaboration group may allow one or more users to share a view for an image data set that is aligned with a body of a person (e.g., patient or subject) and user interface controls and/or user interface information regarding viewing and navigating the image data set. A shared interface may also be provided for users (e.g., medical professionals or doctors) in a collaboration group who are using AR headset technology in medical settings. Specifically, this technology may allow medical professionals to use AR headsets to see the user interface and views of image data set(s) (e.g., slices or the entire image data set) aligned with a patient during a medical procedure, as seen by a selected doctor using a different AR headset. This selected doctor or medical professional may be the designated medical professional for performing a medical procedure. The sharing may allow more than one medical professional to securely share the experience that a selected or designated medical professional is having through the AR headset.

This technology allows a user or joining user to walk into a room (e.g., a medical operating room) and automatically see the user name or actual name of one or more other collaboration users (e.g., people using AR headsets) in the room. These other people may be collaboration users that are in a collaboration group with one or more other collaboration users. The joining user may see that one of the collaboration users is the collaboration leader of the collaboration group, and the collaboration leader of the collaboration group is performing a medical procedure or medical training.

The joining user may access a user interface control (e.g., click a button) with the name of the collaboration user or the user interface control may be near the name, user name or in proximity of a collaboration user as viewed through an AR headset. Further, the joining user may click on the person (or avatar of the person in a remote room as described later) as viewed through the AR headset and the AR headset can detect which person was selected. This may allow the joining user to view a slice of an image data set from the perspective and settings of the collaboration user which was selected. By virtually activating a user interface control on or by a collaboration user (e.g., clicking, pointing or virtually selecting), the joining user can share the current view of the collaboration user from the collaboration user's perspective, or the joining user can switch their view to another collaboration user that is in the collaboration group.

A remote room may also be connected to the room (e.g., medical procedure room or operating room) where a procedure (e.g., medical procedure) is taking place. A joining user or collaboration user in the remote room may want to view what is occurring in the main room or operating room. The remote room can be linked to the main room where the procedure is occurring. The remote room may show virtual reproductions of the users, doctors, patient(s), medical tool(s), the image data set and/or other items in the main room.

Security checks can be applied to determine whether a joining user may or may not join the collaboration group depending on whether the joining user is in the same room as the other collaboration user. This means the system may test to see whether a joining user is in the same physical space as one or more of the collaboration users in the collaboration group. Each of the AR headsets can detect a model of the 3D coordinate space within which the AR headset is located. When a joining user asks to join one or more other collaboration users in a collaboration group then the AR headset of the joining user may report the 3D coordinate space that is being detected by the joining AR headset. The 3D coordinate space from the AR headset of the joining user can be compared to the 3D coordinate space of one or more collaboration users. If the joining user is not in the same space as the other collaboration users, then then joining user cannot join the collaboration group.

For example, the AR headset of the collaboration user can connect to the AR headsets of the joining user to import the joining user's AR headset spatial anchor or topology anchor. If both headsets share the same understanding of the 3D coordinate space, then the joining user may be added to the collaboration space. As an example, if the joining user's 3D coordinate space does not have a high enough level of similarity with the 3D coordinate system of collaboration user(s) in the room, then the joining user cannot join the collaboration group. This means that a user with an AR headset on the other side of the wall of a room may not join a collaboration in the room, even though that AR headset is close in distance to the collaboration group. The comparison between the 3D coordinate spaces of the joining user and the collaboration user may alternatively take place in another computing device or service, such as a server, a cloud server, or a cloud service.

Another aspect of the security may test the proximity of a joining user to a collaboration group using electronic detection or optical detection. A determination of whether the joining user is in proximity of the AR headsets of the collaboration users may be performed using a low power wireless signal. This may provide a distance or proximity test to determine whether a joining user may share in the collaboration group. In one example, the low power wireless signal may be a Bluetooth signal that has 100 feet or less of range. A Bluetooth wireless signal may use low power and the power may be adjusted as desired for the AR headset. By checking that the AR headset is in the same room and can receive or send a Bluetooth signal to an AR headset already in the collaboration group, a joining user may be joined to the collaboration users. This distance test can also find collaboration users (e.g., doctors) in the room with the joining user but generally not in other rooms in the same building or other buildings.

A complex random password may be used to enable the joining of the collaboration group. If the joining user can obtain that password through a Bluetooth broadcast from an AR headset of a collaboration user then the joining user can join the collaboration group. Otherwise, the joining user may not be able to join the collaboration group.

These described security checks may allow a joining user to simply look at and select the collaboration user (i.e., the doctor) in the collaboration group and just connect to the collaboration user without the user having to take active steps to work through security operations, such as entering passwords, using two factor authentication (2FA), etc. However, this system may use other forms of security such as biometrics and 2FA to supplement the described security checks.

In another example, the headset of the joining user may use optical codes. The joining user's AR headset may scan optical codes (e.g., a 2D bar code, a linear bar code, a QR code, an AprilTag, etc.) from another AR headset or optical codes on a collaboration user's person. Information in the optical code (e.g., a password, a key, an identifier, etc.) may automatically be used to gain admittance to the collaboration group.

A remote connection to the collaboration group may allow additional joining users in a remote room to connect to the main room with the collaboration group through a cloud server using a PIN (personal ID number) or code submitted to the cloud server. A remote collaboration user may have their own remote room that is virtually linked to the main room and the AR headset for the remote collaboration user may have a 3D coordinate system for the local room (i.e., remote from the main room) and the collaboration group can map virtual objects, including live virtual avatars for the users in the medical procedure room or operating room, into the remote room. The virtual collaboration users may be able to audibly communicate with the collaboration group using a chat application, a speaker phone, a video chat application or similar audio or video communication systems.

In both the main room situation and remote room situation, a user can enter the room and attempt to join the collaboration group based on being located in the physical room. The joining user will either be the room where the medical procedure is taking place or the joining user will have entered the remote room where another user has already used a meeting ID or PIN to connect the main room and remote room together. When a joining user walks in the main room or the remote room, the joining user may connect to the collaboration group from the respective room because the use of the same room and the close proximity of the joining user to a collaboration user have been verified. More specifically, when a joining user walks into a remote room, then the joining user can join to the collaboration user or person on the virtual session after the security safeguards described earlier are checked.

In one example, once a joining user is verified as being in the local room or remote room, then the joining user may be automatically be joined into the collaboration group in the operating room or the virtual surgical theater. This may occur automatically if one or more of the security criteria are met. The security check may include using the low power wireless connection, optical code recognition and/or 3D coordinate system (e.g., room) recognition. Each user that joins the collaboration group does not have to setup a detailed complex mesh or setup a complex network connection.

The joining user may be connected to a selected AR headset of a person. Alternatively, the AR headset of the joining user may connect to a randomly selected AR headset in order to receive shared state data. In one other example, the AR headset of the joining user may select the AR headset with the highest IP address or lowest IP address and connect with that AR headset. In another example, the joining user may connect to an AR headset based on: a time ordering of AR headsets that joined the collaboration group, which user is the controller of the collaboration group, or other automatic selection criteria, etc.

If a collaboration user with an AR headset drops out of the collaboration group, any AR headsets connected to the AR headset that drops out can re-connect to a different AR headset in the collaboration group. A joining user or collaboration user may connect to any AR headset, as long as each AR headset is connected to the web of AR headsets that form the collaboration group. In one example, the AR headsets may be connected in a tree to avoid any cycles or infinite loops in the messaging structure between the AR headsets.

FIG. 1 illustrates a system 100 for enabling a joining user 130 with an AR headset 132 to share or join a collaboration group 136. There may be one or more collaboration users 102, 120 in the collaboration group 136, for viewing an image data set 108 or a slice of an image data set 104 aligned with a body of a person 110 using AR headsets 106, 122, 132. A topology of a room may be detected using a sensor of the joining user's AR headset. The room may be an operating room 134, a surgical theater, an operating theater, a surgical procedure in an examination room, a surgical tent, or any confined location where a medical procedure is taking place, etc.

The topology of an operating room may include the detection of the walls, floors, ceilings, furniture, objects, tools and other elements in the operating room. The topology detected may be a portion of a room (i.e., it does not need to be the entire room) that can be used for comparison against the recorded topology (a portion or all of a room) of the collaboration user(s). Detecting the topology of the operating room may optionally include detecting humans in the operating room.

The topology of the operating room 134 recorded by the joining user's AR headset 132 may be compared to an operating room topology previously recorded for the collaboration group 136 to determine whether the joining user 130 and the collaboration group 136 are occupying the same operating room 134. The topology of the operating room 134 may have been previously recorded by one of the collaboration users. Alternatively, the topology of the operating room may be a mathematical model of the topology of the operating room created from composite recordings or 3D coordinate system detections from two or more collaboration users in the collaboration group 136. The topology of the operating room detected by the joining user 130 may be sent to a central server 140 or to the AR headset of one or more collaboration users for comparison. An exact topological match may be checked for or the system may check for a match up a certain percentage of confidence (e.g., 75%, 80% or 90% confidence, etc.).

The joining user 130 may be allowed to join the collaboration group 136, based in part on the same operating room being detected. If the probability that the joining user 130 and the collaboration user 120 are in the same operating room exceed a defined probability threshold then the joining user 130 and collaboration user 120 may be considered to be in the same operating room. In addition, the joining user may be allowed to join the collaboration group 136 based on the proximity of the joining user 130 to collaboration user(s) in the collaboration group.

There may be two groups of collaboration users in the collaboration group that are doing two different medical procedures, and these collaboration users may be grouped into separate collaboration groups or collaboration subgroups. A collaboration group or sub-group may be named or have an associated tag based on the procedure that the collaboration user (e.g., a medical professional) is going to perform.

Figure 2:
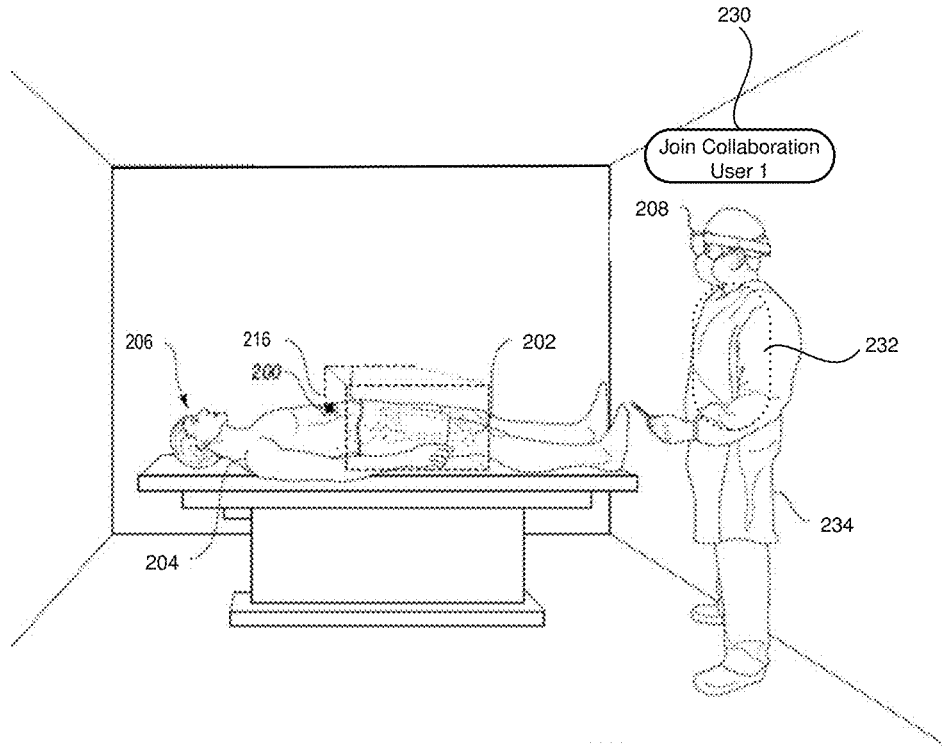
FIG. 2 is a diagram illustrating a user interface for a system and method for enabling a joining user to share a collaboration group.

FIG. 2 illustrates a user interface 230, 232 that may be displayed to allow the joining user to join the collaboration group. A user interface control may be displayed through the AR headset of the joining user, and the user interface control 230, 232 may appear to be associated with a collaboration user 234 of the collaboration group. In one example, a user interface button 230 may appear above the head or in proximity to a collaboration user 234. When the joining user activates the button 230 then the joining user may join the collaboration group of the collaboration user 234. An application or service on the AR headsets 208 (or on a server) may determine that a joining user is going to be allowed to join the collaboration group, after security protocols have been checked. The user interface control for joining a collaboration group may be a button, a selection list with a list of collaboration users, a drop down list with a list of collaboration groups or users, a radio button, a checkbox, a 3D knob, a 3D lever, a 3D graphical control, or any other known 2D or 3D user interface control that can be displayed in the AR headset of the joining user.

In one embodiment, a trigger area 232 (e.g., a detection zone, hitbox or collider) may be created over the body of the collaboration user 234. When the trigger area is selected, the joining process may be activated (e.g., before or after the security check). The trigger area may be a portion of a collaboration user's body 234 (e.g., a head, torso, arm, or hand) that is detectable and visible through the AR headset 208. The portion of the collaboration user's body 234 that becomes a trigger area may even be the entire body of the collaboration user that is detected by the AR headset.

As discussed earlier, a further criterion may be tested or detected to determine whether a joining user may be allowed to join the collaboration group. The system may detect whether the joining user is within physical proximity of or is a limited distance from a collaboration group using electronic detection from the joining user's AR headset. In one example, the electronic detection may detect a short range wireless signal from AR headsets in the collaboration group, or a short range wireless signal may be sent from the AR headset of the joining user to the AR headsets of the collaboration group.

The joining user can be added to the collaboration group when the user interface control is selected, based in part on the electronic detection validating that a same room is being occupied or the joining user is close to the collaboration users. The electronic detection may detect a Bluetooth signal from the collaboration user or a Bluetooth beacon in an operating room. The Bluetooth signal may be sent from a collaboration user's AR headset to the joining user or vice versa and then server or software running on the AR headsets can determine if the joining user has properly sent or received a valid Bluetooth signal.

The joining user may be allowed to join the collaboration group, based in part on the proximity of the joining user to the collaboration group (e.g., the joining user being near to at least one user of the collaboration group as detected using Bluetooth, Bluetooth beacons, or scanned optical codes) and the same operating room is being detected. The joining user may then be allowed to join the collaboration group when the user interface control is selected, based in part on the electronic detection validating that the joining user is close to a collaboration user and the same room is being occupied. One example implementation or use of electronic detection is the detection an optical code from a collaboration user's AR headset or the collaboration user, which validates that the joining user is within sight of the collaboration user and is close enough to scan the optical code associated with one or more collaboration users.

The control of the view and navigation of an image data set 216 that is overlaid on a body of person 206 may be shared between AR headsets 208 using a voice command or a command submitted through a graphical user interface. The collaboration user(s) and joining user's view of the image data set 216 may be using a slice (see 104 in FIG. 1) of the image data set 216 that is aligned with the body 204 of the person 206. For example, the alignment of the image data set 216 with the body 204 of the person 206 may take place using an optical code 200. In addition, a collaboration user 208 may be able to take control of a collaboration group using a voice command.

Returning to FIG. 1, users in a collaboration group 136 may be able to share a collaboration user view of the image data set determined based in part on a position of a selected collaboration user 120 in a 3D coordinate space defined using an AR headset. This means the joining user 130 may see the same view of the slice 104 of the image data set 108 and use the same user interface for navigation of the image data set 108 as one of the collaboration users. The joining user 130 may also determine which of the collaboration users views to use. These types of shared view operations may occur by identifying the joining user 130 with a joining AR headset 132 in the 3D coordinate space. The collaboration user's position in the 3D coordinate space may be sent to the joining user with the joining AR headset 132. This may allow the joining user's view to be set to the collaboration user's view for the image data set 108 through the joining user's AR headset. For example, at least a portion of the image data set 108 may be displayed to the joining user 130 from a perspective that matches the collaboration user 120 view of the image data set. Further, a joining user 130 may control a collaboration user's view of the image data set 108 or navigation. Alternatively, the collaboration user 120 may control the joining user's view of the image data set 108.

In one embodiment, the collaboration user may be in a virtual operating room that is distant from the operating room. Then the joining user may join the collaboration user in the distant or remote operation room (i.e., distant from where the person or patient is located). The collaboration user in the virtual operating room may join the collaboration group by providing an access code to a server configured to transfer collaboration group data to a part of the collaboration group in the virtual operating room. Data representing a state of the collaboration user view may be sent to the AR headset of the joining user. The data may include at least one of: a state of at least one projection slice viewed from a perspective of the collaboration user, a location of the collaboration user in a 3D coordinate space, a depth of at least one projection slice, a medical device location, object locations, or a pointer location.

The collaboration user and the joining user may share user interface functions from their own perspective that are at least one of: altering a position of the image data set in the 3D coordinate system, moving to a different slice in the image data set, rotating a projection slice, or using graphical user interface (GUI) controls from their own perspective. In another configuration, the joining user may perform functions from a perspective of the collaboration user that are at least one of: altering a position of the image data set, dragging to a different slice in the image data set, rotating a projection slice, or using graphical user interface (GUI) controls from the perspective of the joining user.

The system may also allow a joining user to switch to a panel having at least one alternative perspective view of the image data set as defined by the collaboration user view and collaboration user's position. At least one navigational view may be presented to the joining user. The at least one navigation view may be at least one of: a view of the image data set that is orthogonal to the collaboration user view, a custom perspective set by the collaboration user, a defined view of a medical guide, or a defined view that is locked to a body of a person. In addition, the at least one navigation view may include thumbnail views on a user interface bar viewable through the collaboration user's AR headset or joining user's AR headset.

When a joining user is viewing to the AR headset of a collaboration user, the AR headset of the collaboration user may display the name of the user, their remaining battery life, networking information and/or AR headset related information. The joining user may also view the image data set or a slice of the image data set according to collaboration user's perspective or the joining user's perspective. Users may use the command "share from self" to share the view of the image data set from their own perspective. The command "share from self" may provide a slice view of the image data set that is the same slice, same window level, same thickness but from the user's own perspective in the 3D view. This allows the user to follow exactly what another user is doing but view the image data set from their AR headset and perspective, or the user can see the same image slice from the same perspective as the other user. The property of the slice can be set to be facing the user controlling the slice or the primary viewer.

A user can also issue a command to be the collaboration leader of the collaboration group by saying "take ownership of sharing". Then an asterisk, icon or tag may be associated with the user and other users who view the user through their AR headsets will be able to see who the collaboration leader is.

In this technology, the AR headsets do not need to send the video or large amounts of data between the AR headset, but rather the AR headsets send the state information or coordinate information of where a view of the image data set or a slice should originate from. The state data being shared may be anonymized. As a result, the security checks and safeguards may be less rigorous and can be focused on helping users to join the desired collaboration group.

In one example, each doctor in the same 3D coordinate space may see the same view of an image data set from their own perspective. For example, one doctor may slice the image data set (e.g., a CT scan or MRI scan) to create a sagittal view. Then the other doctors in the 3D coordinate space can see the same view (i.e., the same data cut) from the perspectives where they are located. This is useful because the image data may be aligned to the body of a person or patient. Alternatively, the other doctors can see the 3D slice of the image data set from the perspective of the designated doctor, and this view may be at the location where the slice was originally created with a new orientation toward the viewing doctor (of course the slice may not remain aligned with the patient's body in this case). The slice may also be viewed at another location in the 3D coordinate space that is different than where the 3D slice was originally created. The slice may be moved (or translated) to a new coordinate location and may be rotated so that the viewing doctor sees the same view of the slice as the designated doctor.

Joining a collaboration group replicates the 3D experience of one or more users across a 3D coordinate space so each user can be included in the same experiences. This includes sharing of a world view (spatial sharing) and sharing of view of a virtual 3D image data set. The sharing between a group of individuals can be performed without transferring large amounts of data in real-time to each person. The AR headsets transfer: the position from which image data set is being viewed, constraints for viewing the data and a state for viewing the data but the AR headsets do not transfer large amounts of data (e.g., such as CT scans or MRI scans) between the AR headsets.

A joining user may walk into a room (e.g., a surgical theater) and point with their finger or hand at a user in the room with an AR headset and then the joining user may join the experience of the collaboration user selected. The ability to join the user already in the room or collaboration group may be secure as a result of the users being proximate to each other as verified by low power wireless connections, and also because the room topology can be checked to determine if the users are in the same room or a virtually joined room to the physical room.

This technology also allows a user to interactively join a different user that is different than the first user selected. This means the user can switch between the views of different users in the room. For example, a user can switch between collaboration user 1 and collaboration user 2. A user can also join different levels of collaboration. A user can join a space, a collaboration group in a space, join the view of an image data set, or join to a collaboration user (or avatar of the collaboration user in the virtually joined room). The joining user may be able join to view a picture, a video or 3D camera point of view of the person. If the joining user can see and identify another user, then that relationship information is established based on the viewing of the room and the collaboration user.

The AR hardware and processes may track where each AR headset is in the 3D coordinate system and may track a headset pose (e.g., direction the AR headset is looking) in the 3D coordinate system. As described earlier in terms of the joining users and collaboration users, a second AR headset can be used to control the view and navigation for a first AR headset as though the first AR headset is being actually worn by the person wearing the second AR headset and the second AR headset is at the same location as the first AR headset. Because the user of the second AR headset may view the data as though the second AR headset is at the same perspective and position as the first AR headset, then the second user or medical professional may then adjust the spatial positioning, brightness, transparency, slice location, etc. for portions or all of the image data set. These adjustments may also be propagated back to the first AR headset and any other additional AR headsets in the 3D coordinate system that are viewing the image data set. This may mean that a second AR headset can control the other person's view of the image data set through a first AR headset. The first AR headset may also share control of the navigation of the image data set and how the image data set is reconstructed for a user or medical professional to view (e.g., a 3D view, slice view, view orientation, etc.)

In addition, each user or medical professional may be presented with multiple smaller navigation view panels or break-out views that may be inset in the AR headset's view to provide a multi-navigation screen. The navigation views may display a view of the image data set from a perspective that is different than the user's actual view point (e.g., a side view, a mirror image view, a top view, bottom view, etc.).

As mentioned, this technology can transfer the perspective for viewing virtual objects in the AR headsets between separate AR headsets without having to transfer the data contained in a projection of the 3D image data set or without sending video of what one AR headset is seeing or doing to another headset. Sending large graphical data sets can consume a lot of bandwidth and/or use a high speed wired connection. Most operating rooms in the US and especially in foreign countries cannot guarantee high speed wired connections to transfer large graphical data sets or video in real time between AR headsets in the same operating room. Accordingly, transferring the positional data of the AR headsets, an instrument position, the patient orientation, a user interface state, etc. to an attending physician's headset is useful in the training and assistance of other medical professionals. Further, the additional AR headsets may have the alignment of an image data set to a body of a person or patient in the operating room transferred to them so the additional AR headsets do not have to go through the registration and alignment process performed by the first AR headset (or at least one other AR headset).

The present technology further includes a system and method for managing a first user view and a second user view of an image data set aligned with a body of a person using AR headsets. The image data set may be aligned with anatomical structures of the person using at least one marker (e.g., an optical marker) on the person, using morphometrics, using radiopaque markers, or other alignment methods referenced in this disclosure. An image data set can be aligned to the body of the person using a marker or other alignment systems. Medical imaging may be obtained and aligned with a body of a person. For example, a CT (computed tomography) scan, MRI (magnetic resonance imaging) image or other imaging may be overlaid on the patient and used as a reference for aspects of a patient's anatomical structure being operated on. U.S. Pat. Nos. 9,892,564; 10,475,244; 11,004,271; 10,010,379; 10,945,807; 11,266,480; 10,825,563; 11,237,627; 11,287,874; U.S. patent application Ser. No. 17/706,462 entitled "Using Optical Codes with Augmented Reality Displays"; and U.S. patent application Ser. No. 17/536,009 entitled "Image Data Set Alignment for an AR Headset Using Anatomic Structures and Data Fitting"; and U.S. patent application Ser. No. 17/978,962 entitled "3D Spatial Mapping in a 3D Coordinate System of an AR Headset Using 2D Images" describe methods and systems for aligning an image data set from medical imaging devices with a body of a person and these descriptions are incorporated in their entirety by reference herein. An image data set may be aligned to the body of the person using: markers, optical codes, radiopaque markers, 2D imaging, morphometrics or other systems for alignment of 3D image data sets. These patents also describe a wide variety of medical imaging types that may be used to obtain 3D image data sets.

Figure 3:
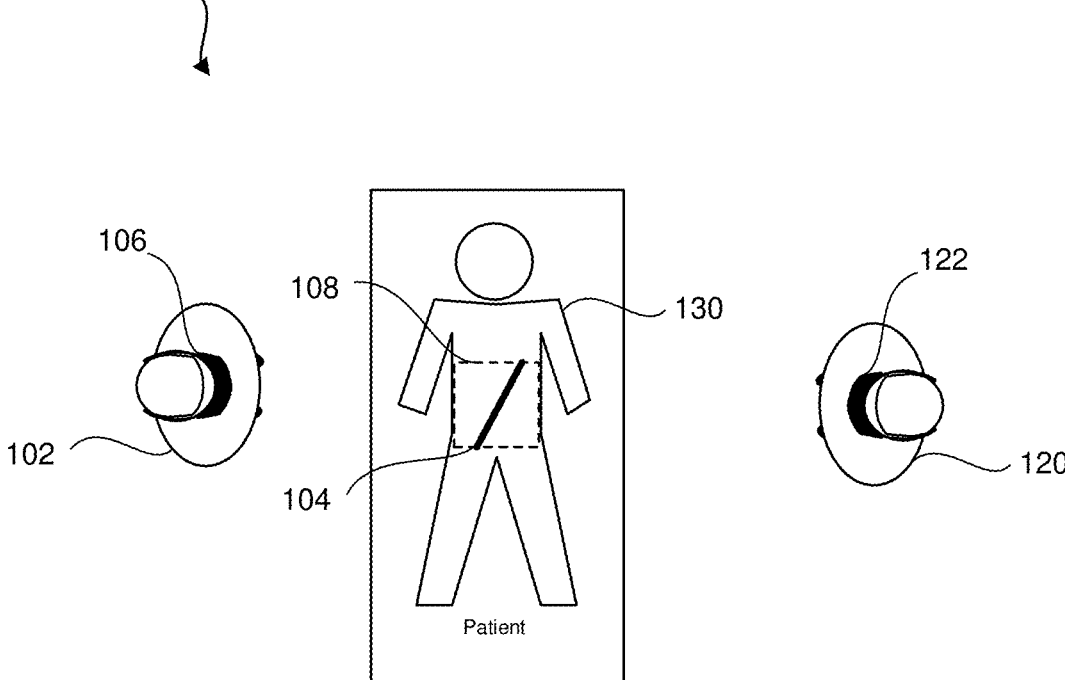
FIG. 3 is a diagram illustrating an example of a system and method for managing a first user view and a second user view of an image data set, where a view of image data set is aligned to a person's body.

FIG. 3 illustrates that a first user view of the image data set 108 may be determined based in part on a position of a first user 102 in a 3D coordinate space 100 as defined using a first AR headset 106. A second user 120 with a second AR headset 122 having a second user view may be identified in the 3D coordinate space 100. The first user view and the second user view may include information about a pose of the AR headset and a coordinate location of the AR headset. Accordingly, the first AR headset and the second AR headset may use a common 3D coordinate system in a location. The 3D coordinate system may be set by a single AR headset or through negotiation of the AR headsets. The location of the AR headsets may be in an operating room, examination room, training room, clinic, hospital room or another location where a medical procedure may be desired to be performed on the body of a person.

The first user's position in the 3D coordinate space with respect to the person may be sent to the second AR headset. The first user's position may be a Cartesian coordinate or another coordinate in the 3D coordinate space (e.g., polar coordinates or another coordinate space system) that is detected using the first AR headset 106.

The second user view 124 of the image data set or other virtual objects may be set to the first user view of the image data set or other virtual objects through the second AR headset. This may mean that second user can see the same 3D slice 104 or projection from the CT scan or MRI scan and the 3D slice may be viewed from the same side so the second user will see the slice in the same way that that the first user is viewing but the 3D slice may not be aligned with the patient's anatomy. The second user may be originally be viewing the 3D slice from a different angle or position than the first user but the first user's viewpoint of the image data set and virtual objects can be transferred to the second user's AR headset.

Figure 4:
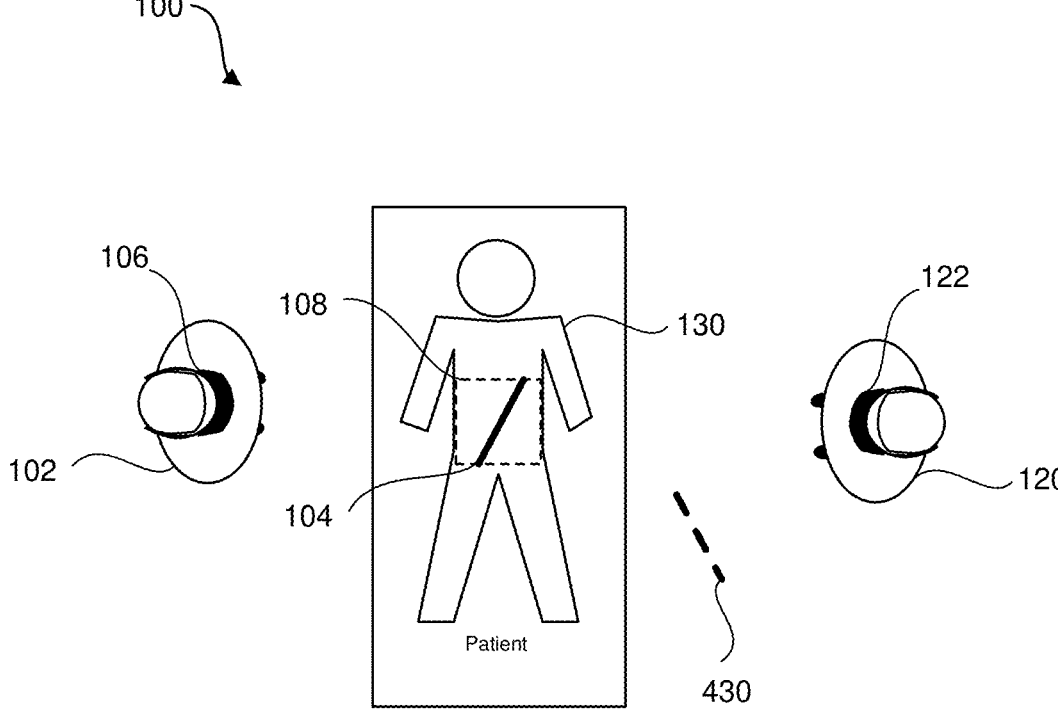
FIG. 4 is a schematic diagram illustrating an example of a system and method for managing a first user view and a second user view of an image data set, where a view of image data set is positioned at a location determined by a user of an AR headset.

In one example, FIG. 4 illustrates that the 3D slice 430 may be presented to the second user but not overlaid on the patient as viewed through the AR headset. The 3D slice 430 may be located in a position that is selected by the second user and the 3D slice 430 may be viewed with the same slice and orientation from the image data set that the first user is using. The 3D slice 430 may be overlaid on the patient, if desired, but the 3D slice 430 may not be aligned with the anatomical features of the patient 430 in order for the second user to view the 3D slice with the same orientation as the first user. The goal can be for the second user to see the virtual view of image data set or other virtual objects that the first user is seeing in the first user's AR headset. More specifically, at least a portion of the image data set may be displayed from a perspective that matches the first user view of the image data set. In one example, the portion of the image data set may be a slice (e.g., 3D slice or a single layer of voxels) from the image data set.

In another example, a first user may be allowed to control a second user view of the image data set or the first user may control navigation of the second user. This means that when the first user moves the 3D slice through the CT scan or MRI scan then the 3D slice will also move for the second user.

In another example, a second user may be allowed to control a first user view of the image data set. If the second user moves the 3D slice by using hand gestures or finger gestures, the view of the 3D slice may be moved for the first user. Any navigation changes made by the second user can be propagated to the first user's AR headset.

Figure 5:
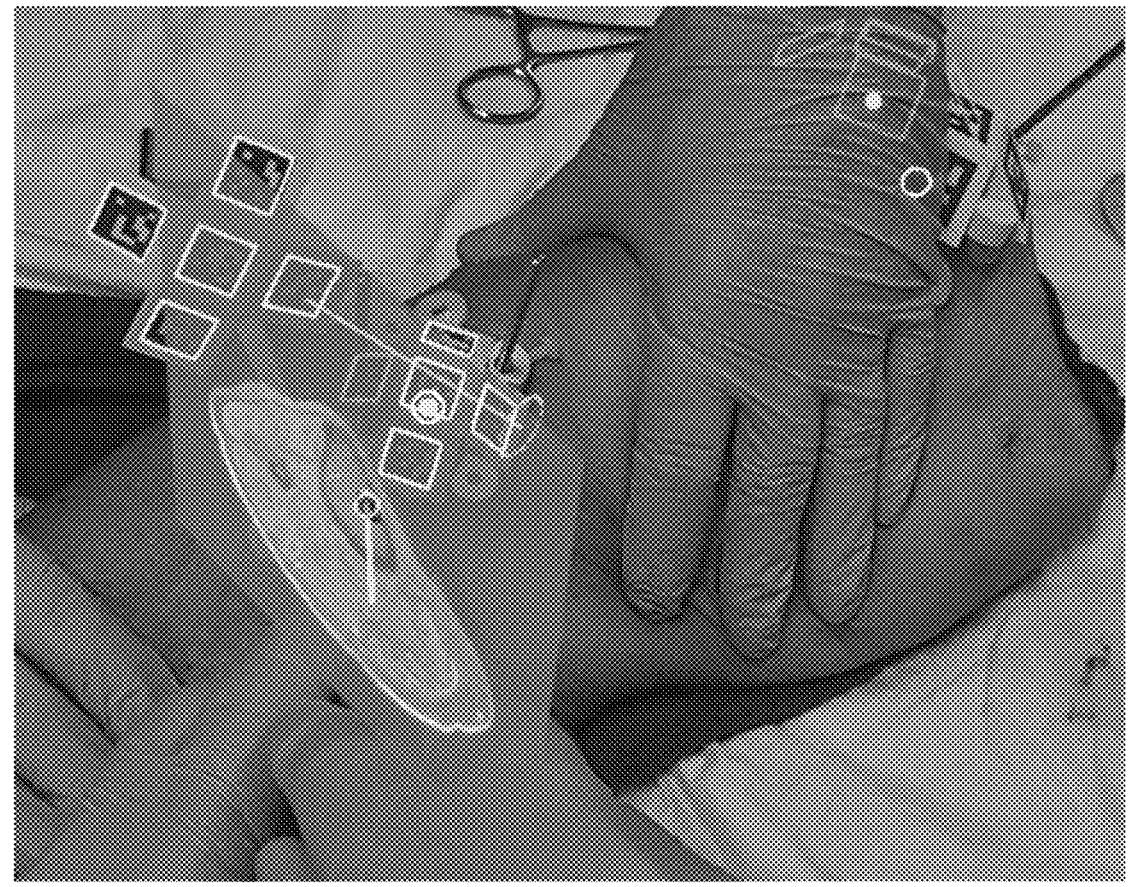
FIG. 5 illustrates an example of a slice of a 3D image data set that may be displayed as an overlay to anatomy.

The user interface may also be configured so that both the first user (e.g., doctor) and the second user (e.g., doctor) can each alter a 3D slice position and orientation, drag the slice through the image data set to see different slice layers, rotate the cut, etc. These shared controls may apply to any number of users or medical professionals in the same 3D coordinate system. The other users or medical professionals who have connected to the primary user's sessions can see the virtual elements in the AR headset from their own perspective or the primary doctor's perspective. FIG. 5 illustrates a slice of the image data set that may be viewed from a first user's perspective, and the use of a medical instrument and representation of a virtual medical instrument (e.g., a burr) on a patient's anatomy (i.e., a cadaver in this image).

Data representing the first user view may also be sent to the second AR headset of the second user, and the data may include one or more viewing details. Examples of these viewing details may include sending information about at least one of: the existence of at least one projection slice viewed from a perspective of the first user, a location of the projection slice, a location of the first user in the 3D coordinate space, a depth of at least one projection slice, a medical device location, object locations, a pointer location, or other virtual object and physical object locations.

In another example of the technology, the first user and the second user may share user interface functions from their own perspectives. A user interface function may include at least one of: altering a position of the image data set in the 3D coordinate system, moving to a different slice in the image data set, rotating a projection slice, changing a projection angle of a slice; identifying a slice of the image data set, and using graphical user interface (GUI) controls from their own perspective. Similarly, the second user may perform functions from a perspective of the first user, including the functions listed above. This means the second user may see what the first user is seeing and be able to do operations like altering a position of the image data set from the first user's perspective, dragging or rotating a slice in the image data set from the first user's perspective, or using graphical user interface (GUI) controls from the perspective of the second user.

In the situation where a first user is using a set of graphical user interface (GUI) controls to perform tasks with respect the image data set that is overlaid on the patient, a copy of these same GUI controls may also be presented to the second user while facing the second user so that the second user can see the things the first using is doing with the GUI interface. For example, if the first user presses virtual button A, then the second user will see their own copy of the interface facing the second user with the virtual button A pushed. Alternatively, the second user may see the first user's interface from a different perspective of the first user. For example, if the first user presses button A, then the second user can see that button A is pressed on the first user's copy of the user interface.

As mentioned earlier, the second user may also view navigation views or alternative perspective views of the image data set. This might include seeing views of the image data set from perspectives that are different than where the second user is actually standing. These views might be a view at an angle to the second user's view, the views may be top and bottom views or other oblique views that may be useful to the medical procedure being undertaken. Accordingly, the second user may switch to or use a panel (e.g., a graphical panel or pane presented in the AR headset) having at least one alternative perspective view of the image data set as defined with respect the second user view and second user's position. Further, at least one navigational view may be presented to the second user. The navigational views may be at least one of: a view of the image data set that is orthogonal to the second user view, a custom perspective defined by the second user, a defined view of a medical guide or medical implement in the medical procedure, or a defined view that is aligned and locked to a body of a person (e.g., an axis of the body of the person). A navigation view may include thumbnail views on a user interface bar viewable through the first AR headset and/or second AR headset.

Figure 6:
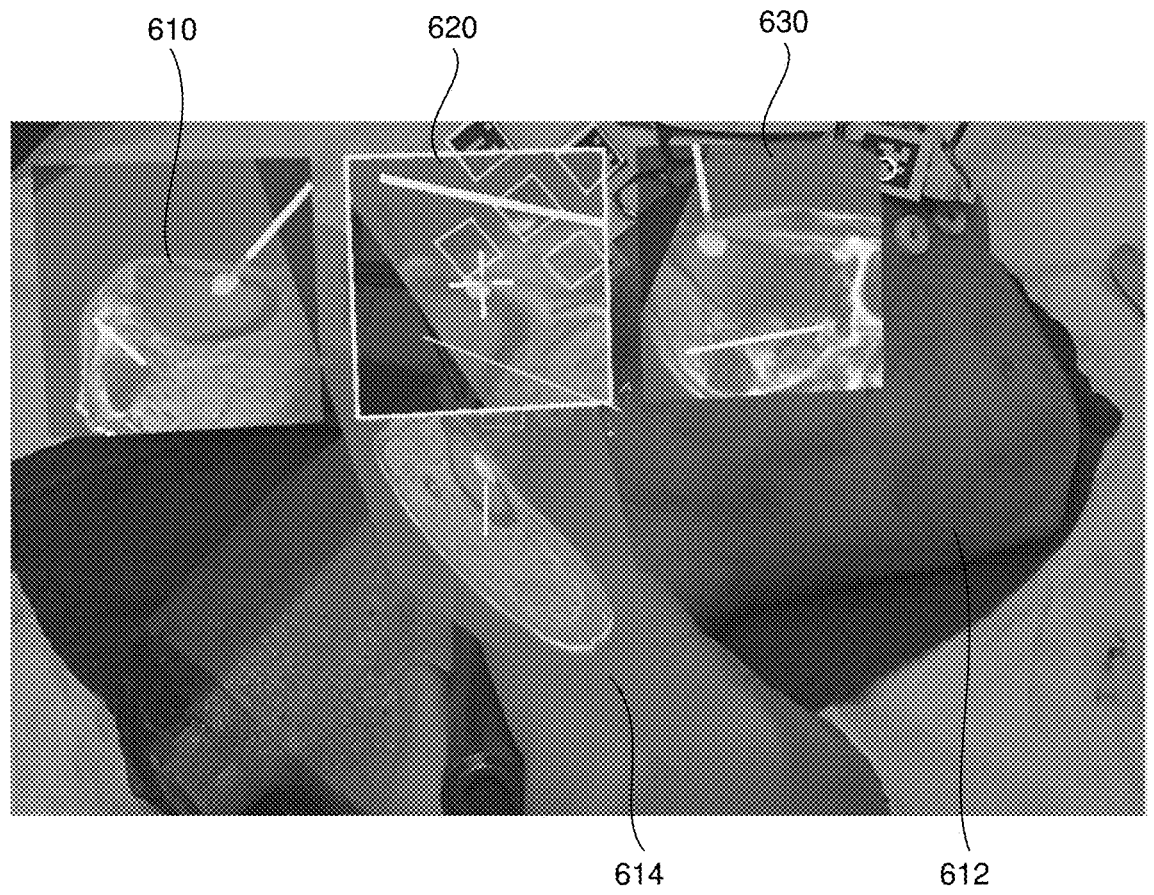
FIG. 6 illustrates an example of a slice of a 3D image data set that may be displayed as an overlay to anatomy and an example navigational view using the AR headset.

FIG. 6 illustrates an example of a slice 614 of a 3D image data set that may be displayed as an overlay to anatomy 612 using the AR headset. A heads up display of multiple breakout views 610, 620, 630 of the X-ray generated images is also displayed. The breakout view may show navigational views of a 3D slice of the 3D image data or the entire image data set desired by a medical professional (e.g., orthogonal to the AR headset view, etc.) as overlays. The breakout views can be navigational views illustrating 3D slices from other perspectives for viewing the overlaid 3D slice. For example, coronal, axial and sagittal views, etc. may be provided.

The navigation (or break-out) views can also be used by a medical professional to tell the medical professional how close they are to a target from a selected perspective. Otherwise, it can be difficult to determine a distance to and orientation of a medical instrument with respect to a target in three dimensions. In one configuration of this technology, the second medical professional may see the break-out view (e.g., in a mini view) from the same perspective as the primary medical professional or first doctor. In another view configuration, the second medical professional can see the primary view and the break-out view from the second medical professional's own perspective. In another alternative, the first and second medical professionals may want to see some of these elements aligned with or locked to the patient anatomy. Then both the first medical professional and second medical professional will see the primary view and/or breakout views the same way regardless of their physical location in the 3D coordinate system of an operating room. The opportunity to set the various views allows the medical professional to individually determine whether they want to see the views from their own perspective in the 3D coordinate system or from the view the primary doctor is currently seeing.

In another example, the second medical professional may select whether they want to see a graphical user interface from the first medical professional's perspective or from their own perspective. This may allow the second medical professional to see a menu or buttons that are their own menu, or the second AR headset of second medical professional can display the first medical professional's menu that is tilted toward the second medical professional. The view of the other medical professional's graphical user interface may also include all the individualized and/or personalized settings that are set for the other medical professional. For instance, allowing a second doctor to see the exact user interface for the first doctor is useful for training, recording, or documenting during the use of the AR headsets.

In another example configuration, the second doctor may see what the first doctor is seeing from a third perspective. The second doctor can set a point in space that is not the first doctor's perspective or the second doctor's perspective but is a third point in space where the doctor would like to view the 3D slices or image data set from.

In yet another configuration, the second medical professional can be contributing to what the first doctor is seeing. Accordingly, the second doctor may see the 3D slice and image data set as though the second doctor is in the place of the first doctor and is moving the needle. In this configuration, the second doctor may also see the first doctor's menus, navigation interface and other graphical user interface controls pointing toward the second doctor.

In a training situation, where two doctors both have AR headset then the second doctor may be trying assist and/or train the first doctor. If the second doctor is training the first doctor, then the second doctor may want to see the virtual overlays in the same way that the first doctor is seeing the virtual overlays. This means the second doctor may see a 3D slice, 3D image data, the first doctor's graphical user interface and/or other virtual objects from the first user's perspective. In addition, when the second doctor makes changes to the 3D slice or 3D image data and the first doctor's user interface, then those changes may be reflected in both the first doctor's and second doctor's views in their AR headsets. In contrast, if a second doctor is assisting a first doctor with a medical procedure but is not training the first doctor, then the second doctor may want to see the 3D slice, 3D image data and the user interface from the second doctor's own perspective.

In this technology, every virtual element that the doctors may interact with can be shared between the different headsets (e.g., two or more headsets). Some elements may be best displayed in one way, such as the 3D data set that is aligned with the anatomical structure of a patient. However, a slice or projection from a 3D data set can also be displayed at different coordinate locations in 3D coordinate system of the AR headset, as described earlier. Other elements in AR headset, such as navigation displays and user interface may be shown in an individualized way for each individual user or doctor based on the configurations described.

There may be at least three perspectives that can be provided to a medical professional:
1. In the first perspective case, the second doctor can see the virtual objects the first doctor is seeing from the first doctor's perspective (see the first doctor's interface and view of virtual overlays using the second doctor's AR headset);
2. In the second perspective case, the second doctor can set the configuration to seeing what the first doctor is doing from second doctor's perspective;
3. In a third perspective case, the second doctor may see their own UI and their own perspective for virtual objects and user interfaces overlaid on the scene.

In prior configurations of AR headsets, AR headsets that are in remote locations (e.g., are geographically separated) are able to share virtual objects that the users of both headsets can view and manipulate. However, in the situation where virtual objects are shared using geographically separate AR headsets, each user is viewing the virtual object from exactly the same perspective as other users. In contrast, the present technology allows users to select which type of virtual object they want to see and the perspective the user wants to see the virtual object from.

For an assisting surgeon there may be virtual items that the assisting surgeon wants to see customized from their own perspective, as opposed to trying to see things from the primary surgeon's (i.e., first doctor's) perspective. This technology is not focusing on remote medical assistance but rather on the training of medical professionals (e.g., surgeons) and the ability for medical professionals to locally cooperate on surgical or medical procedures. This is because the medical professionals sharing the view can be in the same 3D coordinate space as opposed to being in separate locations.

This technology is also different than the sharing of virtual objects that has previously existed in terms of data transfer. The sharing of interfaces between medical professionals in this technology is for training and assisting. There is no need for the AR headsets using the same 3D coordinate space to share bandwidth intensive imaging with each other because any virtual objects or virtual images (e.g., image data sets) do not need to be streamed between the AR headsets. Instead, the AR headsets can retrieve an image data set from a central server or storage location to which the AR headsets are wirelessly and directly connected. Accordingly, the AR headsets of the present technology are not sharing virtual objects or virtual images across a computer network but the processes on the AR headsets can have shared control of: navigation of image data sets, moving of the image data sets, navigation and moving of slices of the image data sets, any other navigation for the image data sets and/or use of the graphical user interface controls. As a further example, the second medical professional's AR headset may send the first medical professional's AR headset: the parameters for a 3D slice that is being viewed, where the first medical professional's instrument should be, a depth for an instrument, a target object, a pointer or virtual instrument, etc. The AR headsets are not sharing objects, but may share navigation data, perspective, and locational data of virtual objects. Immersively and cooperatively navigating through 3D image data from the first doctor's perspective or the second doctor's perspective is different than sharing virtual object data or image data sets between two AR headsets. Instead, this technology can share user interface controls, the coordinates of the controls, the coordinates of the AR headsets, the location of a slice, the slice being viewed, etc.

In the shared view technology, the AR headset can display what portions of an image data set or other virtual objects a first doctor is seeing to a second doctor. The navigation views and the oblique views can also show what the other doctor is seeing. However, the 3D image data set does not need to be streamed to the second doctor for each change in the navigation. The medical imaging data can be loaded independently of the positional or navigation data and prior to the navigation processes. This is because the location of first doctor can be sent to second doctor's headset and the perspective of the first doctor can be used to construct the immersive view for the second doctor.

The settings for the breakout or navigation view can also be sent to the second doctor and those views can be reconstructed or generated at the second AR headset of the second doctor. Thus, the data is being sent as a 3D construct to the AR headsets only one time, and then the AR headset can show the data using the defined perspectives. It is less desirable to try to stream large image data or detailed objects between the AR headsets of individuals located in the same 3D coordinate system. Thus, the image data set can be sent once to each AR headset and then the image data set can be aligned to the body of the patient, but both the first doctor can see the image data set and the second doctor can see the image data set. Either doctor may control how the camera representing both doctors may be flying through or around the image data set, and either doctor can control the image data set. Either of doctors may control where the navigation views are and how the immersive view is presented, what the window level settings are, etc. This results in the streaming of a few kilobytes of positional and navigational data between the AR headsets but not megabytes or gigabytes of data for virtual objects or the 3D image data set. This is because sharing of the navigation instructions and positions of the AR headsets in the 3D coordinate system consume much less data bandwidth than transferring the image data set of the patient. The amount of data sent between two headsets in the same 3D coordinate system may be reduced because the spatial positioning is shared between the two AR headsets and only smaller amounts of information need to shared, including the position of the second AR headset as compared to the first AR headset, using the X, Y, Z position of each AR headset.

In addition, the 3D controls for the breakout views or the navigation views may also be shared in the same ways as described above. For example, the second medical professional may see their own controls for the navigation views or breakout views. Alternatively, the second doctor can see controls for the navigation views or breakout views (and the navigation views themselves) of the first doctor that is being trained or assisted.

In one example, the second doctor can see the 3D image data set from the first doctor's perspective or from the second doctor's own perspective in the 3D coordinate system. The senior surgeon could be training a junior surgeon. The junior surgeon can ask the AR headset to generate a sagittal slice and then create a virtual needle. Then the senior surgeon can show the junior surgeon how to drag the slice and manipulate both the physical needle tip and the virtual needle using the shared view and user interface controls. The senior surgeon may also change the slice thickness, and modify the window level. The junior surgeon may then be shown the target, for instance in the aorta, on their own headset and both the junior surgeon and senior surgeon can see the target marking. This may allow to senior surgeon to correct the views seen and change an incorrect needle insertion position or other incorrect surgical maneuvers. The senior surgeon may watch where the junior surgeon (e.g., resident) is placing the needle and what slice of the image data set is being viewed from their senior surgeon's perspective or the junior surgeon's perspective.

This technology may provide the ability to switch between views of the virtual objects in the 3D coordinate system. The senior surgeon may see one view and the junior surgeon may see another view. Then the senior surgeon may be able to switch between the junior surgeon's view of the virtual objects and/or user interface and their own perspective by toggling a user interface control or selecting a menu item through the AR headset. For instance, the senior surgeon may want to see the navigation views facing the junior surgeon, and then switch to see the navigation views facing the junior surgeon. In the case where there are three (3) or more surgeons in the room (e.g., up to N surgeons) the senior surgeon (or any surgeon with the appropriate permissions) may switch between doctor 1, doctor 2, doctor 3 and doctor N's views or viewing controls.

This technology may be applicable where the junior doctor is trying to navigate an instrument into a 3D object like a spine. If the senior doctor is on the opposing side of the patient, the senior physician (e.g., attending physician) can roughly see what the resident doing. However, what the senior physician really desires to see is if that junior doctor (e.g., resident) is on track to put the needle tip at the right location in the spine in three dimensions. This technology allows the senior doctor to see the same view of the image set data and virtual tool that the junior doctor (e.g., resident) is seeing, so the senior doctor can help adjust or alter the trajectory of the needle or other instrument the junior doctor is controlling. This allows the senior doctor to determine whether the junior doctor is going into or through the right anatomy in the spine.

There are some 3D slice views of the image data set that may look different based on what the medical professional is looking at on the body of patient, particularly where these views are registered to the patient. For views of the image data set that are registered to the patient, these views may have a defined location and orientation in the 3D coordinate system. The example of an axial slice of the image data set that is aligned to the body of the patient will look the same from two opposite sides but flipped. However, an oblique view is typically set to dynamically face the medical professional or user as the medical professional moves around the body of the patient (i.e., the navigation views may be also be facing the user). In the present system, the second doctor may see the exact same view of an oblique view that the first doctor is seeing and the oblique view may not be aligned with the body of the patient for the second viewer. For example, this may mean an oblique view may not align with a patient's anatomical structures for the second doctor.

The second medical professional may also receive (or be sent) the instrument tracking location, regarding where the tip of a needle is in space as controlled by the first medical professional. Instructions can also be sent back and forth to control the view of the 3D or 2D data. For example, the second doctor may control the operation of a fly through for the image data set. Similarly, if the second doctor starts to scroll through slices of the image data set, then the AR headset can start the scrolling view for the first doctor or vice versa. It is not the images, 3D image data sets or virtual objects that are shared between the two AR headsets, it is the coordinate space and current state (e.g., visibility) of the instrument, the patient location, any annotations, any segmentation done, etc. Each medical professional may have the ability to reciprocally control and switch back and forth between the other medical professional's views of virtual objects and their user interface.

This technology may provide a co-pilot feature that may be used between two or more doctors. By analogy, being a single airplane pilot is different than using a dual control plane. The present invention is a dual or multi-control system for an immersive 3D space. The two medical professionals (e.g., co-pilots) who are navigating the virtual overlays in the shared 3D space may be able to share: the 3D registration of the image data set, user interface controls, slicing, a 3D coordinate system, instrument locations and other information for the 3D image data set (e.g., a point cloud of data) they are navigating through.

FIG. 7 illustrates a method for enabling a joining user to share a collaboration group, having at least one collaboration user. The collaboration group can be used for viewing portions of an image data set aligned with a body of a person using AR headsets. One operation in the method may be detecting a topology of an operating room using a sensor of the joining user's AR headset, as in block 710.

Another operation may be comparing the topology of the operating room recorded by the joining user's AR headset to an operating room topology previously or currently being recorded by at least one collaboration user of the collaboration group, as in block 720 This comparison may determine whether the joining user and the collaboration group are occupying the same operating room.

The joining user may be allowed to join the collaboration group, based in part on the same operating room being detected, as in block 730. A user interface control may be displayed through the AR headset of the joining user that appears to be associated with a collaboration user of the collaboration group. The joining user can be added to the collaboration group when the user interface control is selected. The joining user may also be added to the collaboration group based in part on the electronic detection validating that a same room is being occupied by the joining user and the collaboration users. Further, the joining user may be allowed to join the collaboration group, based in part on the proximity of the joining user to the collaboration group and the same operating room being detected.

FIG. 8 illustrates another method for enabling a joining user to share a collaboration group, having at least one collaboration user. The collaboration group may be used for viewing and navigating an image data set aligned with a body of a person using AR headsets.

One operation may be detecting that the joining user is within proximity of a collaboration group using electronic detection from the joining user's AR headset, as in block 810. The electronic detection may use detection of a short range wireless signal from AR headsets in the collaboration group, such as a Bluetooth signal from the collaboration user or a Bluetooth beacon in an operating room. Alternatively, the electronic detection may be scanning of an optical code on a collaboration user or from a collaboration user's AR headset.

A topology of an operating room may also be detected by using a sensor of the joining user's AR headset, as in block 820. The topology of the operating room recorded by the joining user's AR headset may be compared to an operating room topology previously or currently being recorded for the collaboration group to determine whether the joining user and the collaboration group are occupying the same operating room, as in block 830.

The joining user may be allowed to join the collaboration group, based in part on the proximity of the joining user to at least one collaboration user of the collaboration group and the same operating room being detected, as in block 840. A user interface control may be displayed through the AR headset that appears to be associated with a collaboration user of the collaboration group. The joining user can be added to the collaboration group when the user interface control is selected, and based in part on the electronic detection validating the joining user is close to a collaboration user and a same room being occupied.

Once the joining user has joined the collaboration group, the sharing of a view of the image data set may be performed using a voice command. Similarly, a collaboration user can take control of a collaboration group using a voice command.

The users may then share information. For example, a collaboration user view of the image data set may be determined based in part on a position of a collaboration user in a 3D coordinate space defined using a first AR headset. The joining user with a second AR headset may be identified in the 3D coordinate space. The collaboration user's position in the 3D coordinate space with respect to the image data set or joining user may be sent to the second AR headset. Then the joining user view can be set to the collaboration user view of the image data set through the joining user's AR headset. This may allow at least a portion of the image data set to be displayed from a perspective that matches the collaboration user view of the image data set.

A joining user may also be allowed to control a collaboration user view of the image data set or navigation. Alternatively, the collaboration user may be allowed to control the joining user view of the image data set.

This technology allows users of AR headsets to join an experience with aligned graphical medical overlays on a body of a person that is occurring within a collaboration group. This technology may use low power wireless connections, (i.e., Bluetooth or Bluetooth beacons) to determine whether a user is in proximity to the users in a collaboration group. The AR headsets may record the 3D coordinate system for a room viewed by a user and then it may be determined if a joining user is seeing the same room topology as the collaboration users already in the collaboration. The services or software on the headset may import the spatial anchor representing the 3D coordinate space from a joining user and can compare the spatial anchor to another spatial anchor from the at least one collaboration user or a composite 3D coordinate system for the collaboration group. Such a comparison of the 3D coordinate systems may also occur using a server or other computing service.

When the security checks are passed then automated and secure sharing can take place because it is known the users are proximate to each other and have a high probability of being in the same room or same remote room together. This collaborative grouping joins people together in the same immersive physical space with the same virtual elements. This may join the users' spatial world view, 3D image data set views and virtual object views together.

A graphical indicator may be provided to anyone viewing users in the room, and the graphical indicator can represent that two or more users (e.g., two or more doctors) are having the same experience. For example, an icon can be displayed near each user showing an identifier such as "Collaboration User 1", a colored icon or a picture of the controlling user. Another user (another doctor) may be having a different experience and may have no graphical indicator or their own graphical indicator representing their experience or their own group.

FIG. 9 is a flowchart illustrating a method for managing a first user view and a second user view of an image data set aligned with a body of a person (e.g., using at least one marker on a person or another alignment method) and AR headsets. One operation of the method may be determining the first user view of the image data set based in part on a position of a first user in a 3D coordinate space defined using a first AR headset, as in block 910.

A second user with a second AR headset in the 3D coordinate space may be identified, as in block 920. The first AR headset and the second AR headset may be using a common 3D coordinate system in a location or operating room. The system may be configured to let the second user and second AR headset share the virtual view, user interface controls, navigation controls or any other user interface controls and virtual aspects with the first user. The first user's position in the 3D coordinate space with respect to the person may be sent to the second AR headset, as in block 930.

The second user view can be set to the first user view of the image data set through the second AR headset, as in block 940. The second AR headset can use the 3D coordinate position of the first user to provide the view of the image data set to the second AR headset, where the view of the image data set displayed by the second AR headset may match the first headset. For example, at least a portion of the image data set can be displayed from a perspective that matches the first user view of the image data set. The portion of the image data set may be a slice of samples or voxels (e.g., at least one layer) from the image data set.

The second user may also be able to control the first user's interface for viewing and navigation of the image data set that is overlaid on a patient through the AR headset. This may include switching to a control interface of the first user to enable viewing and control of the image data set using the control interface of the first user. A representation of the first user view may be sent to the second AR headset of the second user. The representation may include instructions regarding at least one of: identifying at least one 3D slice viewed from a perspective of the first user, a location of the first user in the 3D coordinate space, a depth of at least one projection slice, a medical device location, instrument locations, virtual object locations, virtual instruments, or a pointer location.

The first user and the second user may be able to share user interface functions from their own perspective. These shared user interface functions may be at least one of: altering a position of the image data set in the 3D coordinate system, moving to a different slice in the image data set, rotating a projection slice and using graphical user interface (GUI) controls from their own perspective. Similarly, the second user may perform functions from a perspective of the first user, including at least one of: altering a position of the image data set, dragging to a different slice in the image data set, changing the slice position, rotating a projection slice, and using graphical user interface (GUI) controls from the perspective of the second user.

In another configuration, the second user view may switch to a panel having at least one alternative perspective view (i.e., navigation views) of the image data set as defined by the first user view and first user's position. As a result, one or more additional navigational views of the first user are presented to the second user. The additional navigation views may include at least one of: a view of the image data set that is orthogonal to the first user view, a custom perspective set by the first user, a defined view of a medical guide, or a defined view that is locked to a body of a person. The navigation view may include thumbnail views on a user interface bar viewable through the first AR headset or second AR headset.

Figure 10:
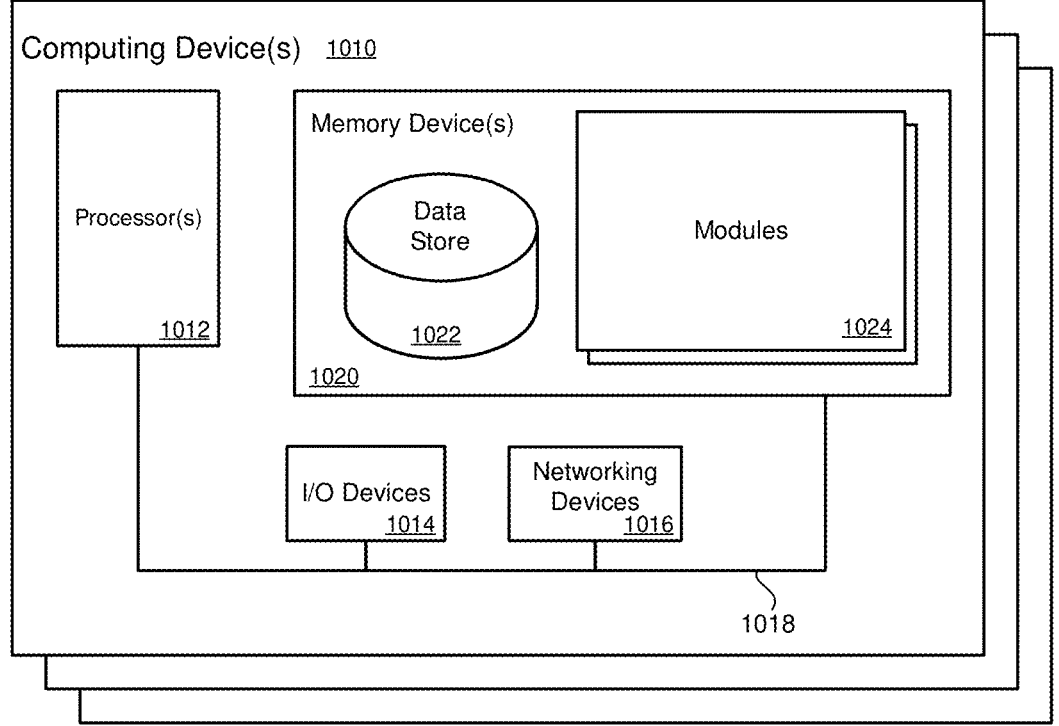
FIG. 10 is a block diagram that provides an example illustration of a computing device that may be employed in the present technology.

FIG. 10 illustrates a computing device 1010 on which modules of this technology may execute. The computing device 1010 is illustrated on which a high level example of the technology may be executed. The computing device 1010 may include one or more processors 1012 that are in communication with memory devices 1020. The computing device may include a local communication interface 1018 for the components in the computing device. For example, the local communication interface may be a local data bus and/or any related address or control busses as may be desired.

The memory device 1020 may contain modules 1024 that are executable by the processor(s) 1012 and data for the modules 1024. The modules 1024 may execute the functions described earlier. A data store 1022 may also be located in the memory device 1020 for storing data related to the modules 1024 and other applications along with an operating system that is executable by the processor(s) 1012.

Other applications may also be stored in the memory device 1020 and may be executable by the processor(s) 1012. Components or modules discussed in this description that may be implemented in the form of software using high level programming languages that are compiled, interpreted or executed using a hybrid of the methods.

The computing device may also have access to I/O (input/output) devices 1014 that are usable by the computing devices. An example of an I/O device is a display screen that is available to display output from the computing devices. Other known I/O device may be used with the computing device as desired. Networking devices 1016 and similar communication devices may be included in the computing device. The networking devices 1016 may be wired or wireless networking devices that connect to the internet, a LAN, WAN, or other computing network.

The components or modules that are shown as being stored in the memory device 1020 may be executed by the processor 1012. The term "executable" may mean a program file that is in a form that may be executed by a processor 1012. For example, a program in a higher level language may be compiled into machine code in a format that may be loaded into a random access portion of the memory device 1020 and executed by the processor 1012, or source code may be loaded by another executable program and interpreted to generate instructions in a random access portion of the memory to be executed by a processor. The executable program may be stored in any portion or component of the memory device 1020. For example, the memory device 1020 may be random access memory (RAM), read only memory (ROM), flash memory, a solid state drive, memory card, a hard drive, optical disk, floppy disk, magnetic tape, or any other memory components.

The processor 1012 may represent multiple processors and the memory 1020 may represent multiple memory units that operate in parallel to the processing circuits. This may provide parallel processing channels for the processes and data in the system. The local interface 1018 may be used as a network to facilitate communication between any of the multiple processors and multiple memories. The local interface 1018 may use additional systems designed for coordinating communication such as load balancing, bulk data transfer, and similar systems.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A method for enabling a joining user to share a collaboration group, having at least one collaboration user, for viewing at least a portion of an image data set aligned with a body of a person using AR headsets, comprising:
  detecting a topology of an operating room using a sensor of the joining user's AR headset;
  comparing the topology of the operating room recorded by the joining user's AR headset to an operating room topology previously recorded for at least one collaboration user of the collaboration group to determine whether the joining user and the collaboration group are occupying a same operating room; and
  allowing the joining user to join the collaboration group, based in part on the same operating room being detected.

2. The method as in claim 1, further comprising:
  displaying a user interface control through the AR headset that appears to be associated with a collaboration user of the collaboration group; and
  adding the joining user to the collaboration group when the user interface control is selected, based in part on electronic detection validating the same operating room is being occupied.

3. The method as in claim 1, further comprising allowing the joining user to join the collaboration group, based in part on proximity of the joining user to the collaboration group and the same operating room being detected.

4. The method as in claim 1, further comprising:
  detecting that the joining user is within proximity of a collaboration group using electronic detection from the joining user's AR headset, using the joining user's AR headset; and
  allowing the joining user to join the collaboration group, based in part on the proximity of the joining user to the collaboration group and the same operating room being detected.

5. The method as in claim 4, further comprising:
  displaying a user interface control through the AR headset that appears to be associated with a collaboration user of the collaboration group; and
  adding the joining user to the collaboration group when the user interface control is selected, based in part on the electronic detection validating the joining user is close to a collaboration user and the same operating room is being occupied.

6. The method as in claim 4, wherein the electronic detection uses detection of a short range wireless signal from AR headsets in the collaboration group.

7. The method as in claim 6, wherein the electronic detection is detecting a Bluetooth signal from the collaboration user or a Bluetooth beacon in an operating room.

8. The method as in claim 4, wherein the electronic detection is scanning of an optical code from a collaboration user's AR headset.

9. The method as in claim 1, further comprising enabling sharing of the image data set using a voice command.

10. The method as in claim 1, further comprising enabling a collaboration user to take control of the collaboration group using a voice command.

11. The method as in claim 1, further comprising:

determining a collaboration user view of the image data set based in part on a position of a collaboration user in a 3D coordinate space defined using a first AR headset;

identifying the joining user with a second AR headset in the 3D coordinate space;

sending the collaboration user's position in the 3D coordinate space with respect to the joining user to the second AR headset; and setting the joining user view to the collaboration user view of the image data set through the joining user's AR headset.

12. The method as in claim 1, further comprising displaying at least a portion of the image data set from a perspective that matches the collaboration user view of the image data set.

13. The method as in claim 1, further comprising allowing a joining user to control a collaboration user view of the image data set or navigation.

14. The method as in claim 1, further comprising allowing the collaboration user to control the joining user view of the image data set.

15. A method for enabling a joining user to share a collaboration group, having at least one collaboration user, for viewing at least a portion of an image data set aligned with a body of a person using AR headsets, comprising:

detecting that the joining user is within proximity of a collaboration user of a collaboration group using electronic detection of a wireless signal from a collaboration user's AR headset, using the joining user's AR headset;

displaying a user interface control associated with the collaboration user in the collaboration group using the joining user's AR headset, based in part on the proximity of the joining user to the collaboration group; and enabling the joining user to join the collaboration group when the user interface control is selected using input received using the joining user's AR headset.

16. The method as in claim 15, wherein the electronic detection uses detection of a short range wireless signal from AR headsets in the collaboration group.

17. The method as in claim 15, wherein the electronic detection is detecting a low power wireless signal from the collaboration user or a wireless beacon in an operating room.

18. The method as in claim 16, wherein the electronic detection is detecting a Bluetooth signal from the collaboration user or a Bluetooth beacon in an operating room.

19. The method as in claim 15, further comprising:

detecting a topology of an operating room using a sensor of the joining user's AR headset;

comparing the topology of the operating room recorded by the joining user's AR headset to an operating room topology previously recorded for the collaboration group to determine whether the joining user and the collaboration group are occupying a same operating room; and enabling the joining user to join the collaboration group when the user interface control is selected, based in part on the proximity of the joining user to the collaboration group and the same operating room being detected.

20. The method as in claim 15, further comprising:

displaying the user interface control through the AR headset that appears to be associated with a collaboration user of the collaboration group; and adding the joining user to the collaboration group when the user interface control is selected, wherein the electronic detection validates the joining user is close to a collaboration user and a same operating room is occupied by the joining user and the collaboration group.

21. The method as in claim 15, wherein the electronic detection is scanning of an optical code from a collaboration user's AR headset.

22. The method as in claim 15, wherein the collaboration user is in a virtual operating room that is distant from the operating room.

23. The method as in claim 22, wherein the collaboration user in the virtual operating room joins the collaboration group by providing an access code to a server configured to transfer collaboration group data to a portion of the collaboration group in the virtual operating room.

24. A method for enabling a joining user to share a collaboration group, having at least one collaboration user, for viewing an image data set aligned with a body of a person using AR headsets, comprising:

detecting that the joining user is within proximity of a collaboration group using electronic detection from the joining user's AR headset, using the joining user's AR headset;

detecting a topology of an operating room using a sensor of the joining user's AR headset;

comparing the topology of the operating room recorded by the joining user's AR headset to an operating room topology previously recorded for the collaboration group to determine whether the joining user and the collaboration group are occupying the same operating room; and allowing the joining user to join the collaboration group, based in part on the proximity of the joining user to the collaboration group and the same operating room being detected.

25. The method as in claim 24, further comprising:

displaying a user interface control through the AR headset that appears to be associated with a collaboration user of the collaboration group; and adding the joining user to the collaboration group when the user interface control is selected, based in part on the electronic detection validating the joining user is close to a collaboration user and the same operating room is being occupied.

26. The method as in claim 24, wherein the electronic detection uses detection of a short range wireless signal from AR headsets in the collaboration group.

27. The method as in claim 26, wherein the electronic detection is detecting a Bluetooth signal from the collaboration user or a Bluetooth beacon in an operating room.

28. The method as in claim 24, wherein the electronic detection is scanning of an optical code from a collaboration user's AR headset.

29. The method as in claim 24, further comprising enabling sharing of the image data set using a voice command.

30. The method as in claim 24, further comprising enabling a collaboration user to take control of the collaboration group using a voice command.

31. The method as in claim 24, further comprising:

determining a collaboration user view of the image data set based in part on a position of a collaboration user in a 3D coordinate space defined using a first AR headset;

identifying the joining user with a second AR headset in the 3D coordinate space;

sending the collaboration user's position in the 3D coordinate space with respect to the joining user to the second AR headset; and setting the joining user view to the collaboration user view of the image data set through the joining user's AR headset.

32. The method as in claim 24, further comprising displaying at least a portion of the image data set from a perspective that matches the collaboration user view of the image data set.

33. The method as in claim 24, further comprising allowing a joining user to control a collaboration user view of the image data set or navigation.

34. The method as in claim 24, further comprising allowing the collaboration user to control the joining user view of the image data set.

35. The method as in claim 24, wherein data representing the collaboration user view is sent to the AR headset of the joining user including at least one of:

at least one projection slice viewed from a perspective of the collaboration user, a location of the collaboration user in a 3D coordinate space, a depth of at least one projection slice, a medical device location, object locations; or a pointer location.

36. The method as in claim 24, wherein the collaboration user and the joining user share user interface functions from their own perspective that are at least one of:

altering a position of the image data set in a 3D coordinate system, moving to a different slice in the image data set, rotating a projection slice, or using graphical user interface (GUI) controls from their own perspective.

37. The method as in claim 24, wherein the joining user performs functions from a perspective of the collaboration user that are at least one of:

altering a position of the image data set, dragging to a different slice in the image data set, rotating a projection slice, or using graphical user interface (GUI) controls from the perspective of the joining user.

38. The method as in claim 24, further comprising switching to a panel having at least one alternative perspective view of the image data set as defined by the collaboration user view and collaboration user's position.

39. The method as in claim 24, wherein at least one navigational view is presented to the joining user.

40. The method as in claim 39, wherein the at least one navigation view may be at least one of: a view of the image data set that is orthogonal to the joining user view, a custom perspective set by the joining user, a defined view of a medical guide, or a defined view that is locked to a body of a person.

41. The method as in claim 39, wherein the at least one navigation view includes thumbnail views on a user interface bar viewable through the collaboration user's AR headset or joining user's AR headset.

42. A system for enabling a joining user to share a collaboration group, having at least one collaboration user, for viewing an image data set aligned with a body of a person using AR headsets, comprising:

at least one processor;

at least one memory device including a data store to store a plurality of data and instructions that, when executed, cause the system and processor to:

detect that the joining user is within proximity of a collaboration group using electronic detection from the joining user's AR headset;

detect a topology of an operating room using a sensor of the joining user's AR headset;

compare the topology of the operating room recorded by the joining user's AR headset to an operating room topology previously recorded for the collaboration group to determine whether the joining user and the collaboration group are occupying the same operating room;

display a user interface control through the AR headset that appears to be in proximity to a collaboration user of the collaboration group; and adding the joining user to the collaboration group when the user interface control is selected, wherein the electronic detection validates the joining user is close to a collaboration user, and the same operating room is being occupied.

43. The system as in claim 42, wherein the electronic detection uses detection of a short range wireless signal from AR headsets in the collaboration group.

44. The system as in claim 43, wherein the electronic detection is detecting a Bluetooth signal from the collaboration user or a Bluetooth beacon in an operating room.

45. The system as in claim 42, wherein the electronic detection is scanning of an optical code from a collaboration user's AR headset.

* * * * *